(12) United States Patent
Park et al.

(10) Patent No.: US 11,185,248 B2
(45) Date of Patent: Nov. 30, 2021

(54) MRI APPROACH OF MULTIPLE TIMES TO REPEAT FOR DETECTION OF NEURONAL OSCILLATIONS

(71) Applicant: Korea Advanced Institute of Science and Technology, Daejeon (KR)

(72) Inventors: Sung-Hong Park, Daejeon (KR); Kihwan Kim, Daejeon (KR); Hyoim Heo, Daejeon (KR); Hyun-Soo Lee, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 559 days.

(21) Appl. No.: 15/947,418

(22) Filed: Apr. 6, 2018

(65) Prior Publication Data

US 2018/0289282 A1  Oct. 11, 2018

(30) Foreign Application Priority Data

Apr. 11, 2017 (KR) .................. 10-2017-0046795
Mar. 6, 2018 (KR) .................. 10-2018-0026216

(51) Int. Cl.
*A61B 5/055* (2006.01)
*A61B 5/00* (2006.01)
*G01R 33/48* (2006.01)

(52) U.S. Cl.
CPC ............ *A61B 5/055* (2013.01); *A61B 5/0042* (2013.01); *A61B 5/4064* (2013.01);
(Continued)

(58) Field of Classification Search
CPC ..... A61B 5/0042; A61B 5/055; A61B 5/4064; A61B 5/7203; A61B 5/7257; G01R 33/4806
See application file for complete search history.

(56) References Cited

U.S. PATENT DOCUMENTS 9,921,280 B2   3/2018   Kim et al.
10,254,365 B2  4/2019   Park et al.
(Continued)

FOREIGN PATENT DOCUMENTS

EP    2975424 A1   1/2016
JP    2000-321123 A  11/2000
(Continued)

OTHER PUBLICATIONS

Notice of Allowance issued in corresponding Korean Patent Application No. 10-2018-0026216, dated Aug. 9, 2019 with partial translation (3 Pages).

*Primary Examiner* — Mark D Remaly
(74) *Attorney, Agent, or Firm* — Osha Bergman Watanabe & Burton LLP

(57) ABSTRACT

Disclosed are a method of detecting a neuron resonance signal and an MRI signal processing apparatus. The method of detecting a neuron resonance signal includes acquiring a plurality of different digital sequences respectively corresponding to a plurality of different repetition periods by sampling a magnetic resonance signal of a neuron resonance signal according to each of the plurality of different repetition periods and calculating correlation between the plurality of different digital sequences in a frequency band based on the plurality of different digital sequences.

14 Claims, 18 Drawing Sheets

(52) U.S. Cl.
CPC ........ *G01R 33/4806* (2013.01); *A61B 5/7203* (2013.01); *A61B 5/7257* (2013.01)

(56) References Cited

U.S. PATENT DOCUMENTS

| | | |
|---|---|---|
| 2004/0095139 A1 | 5/2004 | Brown |
| 2014/0343397 A1 | 11/2014 | Kim et al. |
| 2015/0238112 A1* | 8/2015 | Park .................. G01R 33/4806 600/410 |
| 2016/0033600 A1 | 2/2016 | Lee et al. |
| 2016/0170002 A1 | 6/2016 | Park et al. |
| 2017/0053402 A1 | 2/2017 | Migukin et al. |
| 2017/0322273 A1* | 11/2017 | Truong .............. G01R 33/4806 |

FOREIGN PATENT DOCUMENTS

| | | |
|---|---|---|
| JP | 5718148 B2 | 5/2015 |
| KR | 10-2004-0044155 A | 5/2004 |
| KR | 10-1297143 B1 | 8/2013 |
| KR | 10-1310750 B1 | 9/2013 |
| KR | 10-2015-0125543 A | 11/2015 |
| KR | 10-2016-0015105 A | 2/2016 |
| KR | 10-2016-0071230 A | 6/2016 |
| KR | 10-1683217 B1 | 12/2016 |
| WO | 2007-062255 A2 | 5/2007 |

\* cited by examiner (a)

(b)

(a)           (b)

MRI APPROACH OF MULTIPLE TIMES TO REPEAT FOR DETECTION OF NEURONAL OSCILLATIONS

CROSS-REFERENCE TO RELATED APPLICATIONS

This application claims priority from Korean Patent Application No. 10-2017-0046795, filed on Apr. 11, 2017, in the Korean Intellectual Property Office, and Korean Patent Application No. 10-2018-0026216, filed on Mar. 6, 2018, in the Korean Intellectual Property Office, the disclosure of which is incorporated herein by reference in its entirety.

BACKGROUND OF THE INVENTION

Field of the Invention

Apparatuses and methods consistent with the present invention relate to magnetic resonance imaging (MRI) data acquisition and processing techniques for neuronal resonance magnetic resonance imaging, and more particularly, to a technique of processing MRI data of neuronal resonance MRI by measuring a size of a neuronal resonance signal using two or more repetition times.

Description of the Related Art

In recent system biology research, a hypothesis that communication between brain regions are selectively performed from the brain's entire signal through a selective frequency band filter has been proposed. The technique of measuring a resonance frequency of neurons for communication between brain regions based on this hypothesis may reveal the mechanism of communication between brain regions that are not well known at present and enormously affect brain researches including psychology, mental science, and pathology.

The brain is made up of small regions responsible for numerous functions, and these brain regions are structurally connected to each other. Most brain functions, such as behavior, cognition, and perception, are made by reassembling the brain's network quickly and flexibly. Recent studies have revealed that vibrations and synchronization of neurons occurring in a particular frequency band control flow of information between brain regions which are structurally connected and enable flexible and selective communication between brain regions. However, it is not clear that, in which mechanism, selective and flexible communication of the brain fitting a specific frequency band is made in a dormant state and active/stimulated state. Moreover, a number of clinical data indicates that patients with brain diseases such as autism, schizophrenia, epilepsy, dementia, and Parkinson's disease have altered synchronization characteristics of neurons in a broad frequency band and such abnormal neuronal synchronization may cause symptoms of the diseases (abnormal perception, behavior, motion, etc.).

Therefore, understanding the selective inter-brain region communication mechanism through synchronization may discover a very important clue in a treatment of biopathology and brain diseases. Furthermore, development of a new imaging technique that is able to map the resonance characteristics of neurons to high resolution for a wide frequency band used for communication between brain regions may bring about a great ripple effect in academia, industrial circles, and medical community related to biomedical engineering.

Meanwhile, functional magnetic resonance imaging (fMRI) indirectly measures brain activity by an interaction between neurons and bloodstream rather than directly measuring it through a current of neurons. Unlike the conventional MRI, fMRI is a technology that repeatedly acquires images during and before and after external stimuli and maps brain regions correlated with temporal patterns of the corresponding external stimuli through statistical processing. fMRI is a special imaging technique capable of noninvasively mapping of neuronal activity, but it uses indirect measurement through a change in blood flow based on neuronal activity rather than direct measurement of electrical signals of neurons.

Meanwhile, some study indicates that fMRI may be performed even without external stimulation. This new fMRI technology is called resting-state fMRI. A basic assumption of the resting-state fMRI starts from the fact that if two regions of the brain are functionally related, temporal MRI signal changes will also correlate. Resting-state fMRI measures functional connectivity between brain regions.

However, existing fMRI techniques, including the resting-state fMRI, indirectly measure neurons' activity through hemodynamic responses in a local region. The hemodynamic response is slow and has time delay of about 4 seconds. The resting-state fMRIs show functional connectivity between brain regions but they do not show in which mechanism brain regions selectively communicate with each other. This is a fundamental limitation of the existing fMRI technique and explains why "resonance of frequency-selective neurons" cannot be confirmed by conventional methods.

The method of measuring a current of neurons directly by MRI has been continuously tried. However, many researchers argue that an MRI signal generated due to a change in magnetic field generated by a current in neurons is too small to be consistently measured in vivo by MRI. There are two types MRI imaging methods to directly detect an electrical signal of neurons. One method is giving a periodic stimulus with a certain time interval and measuring an electrical signal of neurons by immediately acquiring an MRI signal as soon as each stimulus ends (i.e., before a hemodynamic response occurs). Another method is increasing temporal resolution of MRI image acquisition ($\leq 100$ ms) to find a component tuned with a frequency of an external stimulus through Fourier transform. Both methods depend on a cycle or a frequency of the external stimulus and do not take a natural frequency of neurons into consideration. With respect to all the existing MRI imaging techniques including the aforementioned two methods, whether a current signal of neurons is detected is still controversial.

Korean Patent Registration No. 10-1683217 discloses a neuron resonance magnetic resonance imaging method as a new technique for solving the above-described problems. According to this technique, a signal of neurons may be maximized by applying an oblique magnetic field pattern oscillating according to a resonance frequency of neurons to an MRI imaging technique. Also, this technique may solve a problem that an MRI signal based on a current of neurons is very small and a problem that a temporal interval and phase randomly occur in a neuronal resonance shape, by extracting a component corresponding to the resonance frequency of neurons through the Fourier analysis method after repeatedly performing multi-phase image acquisition. The above-described technique may not only extract a signal of neurons in a frequency-selective manner by using a repetitive multi-phase image acquisition method and the Fourier analysis method but also significantly improves a signal-to-noise (S/N) ratio through a temporal averaging effect. In addition, it may complete a communication channel map for each frequency band between brain regions, which is not possible in the related art, and provide a basic technology for recognizing specific frequencies related to brain functions and brain diseases and the corresponding brain regions. In this technique, however, in order to detect a magnetic field oscillation signal, a process of acquiring MRI data must be repeatedly performed by an MRI imaging technique using an oblique magnetic field pattern a plurality of times, having a technical restriction in that a relative phase between the oblique magnetic field pattern and the magnetic field oscillation signal must be changed. In addition, this technique has drawbacks in that a neuron resonance signal may be extracted at the time when the neuron resonance signal can be predicted.

SUMMARY OF THE INVENTION

Exemplary embodiments of the present invention overcome the above disadvantages and other disadvantages not described above. Also, the present invention is not required to overcome the disadvantages described above, and an exemplary embodiment of the present invention may not overcome any of the problems described above.

The present invention provides a technique for revealing a frequency-selective inter-brain region communication mechanism based on systematic biological research into frequency-selective inter-brain region communication mechanism. The present invention also provides a proof-of-concept experiment and a technique that is useful for completing a frequency-selective entire inter-brain region communication map.

The present invention also provides a technique of processing data of a neuronal resonance magnetic resonance imaging (MRI) by measuring a magnitude of a neuronal resonance signal using a plurality of repetition times (or a repetition period).

The present invention also provides a technique of identifying a frequency component of a neuronal resonance signal based on sampling data of a magnetic resonance signal of a neuron resonance signal according to a plurality of repetition times (or a repetition period) even when the neuron resonance signal cannot be predicted.

According to an aspect of the present invention, a method of detecting a neuron resonance signal includes: acquiring a plurality of different digital sequences respectively corresponding to a plurality of different repetition periods by sampling a magnetic resonance signal of a neuron resonance signal according to each of the plurality of different repetition periods; and calculating correlation between the plurality of different digital sequences in a frequency band based on the plurality of different digital sequences.

The method may further include: identifying a frequency component in which a magnitude of the calculated correlation is equal to or greater than a predetermined magnitude, as a frequency component of the neuron resonance signal.

The calculating may include calculating the correlation by transforming each of the plurality of different digital sequences into a frequency band and superpositioning the plurality of different digital sequences of the transformed frequency bands.

The calculating may include calculating the correlation by convoluting the plurality of different digital sequences and transforming the convoluted digital sequences into frequency bands.

The calculating may include setting a certain resonance frequency and calculating the correlation based on the set certain resonance frequency, a phase difference between each of the plurality of different repetition periods, and data of each of the plurality of acquired different digital sequences.

The method may further include: padding dummy data to each of the plurality of acquired different digital sequences to become a preset sampling period.

The dummy data may be 0, a predetermined constant, or a value acquired by interpolating data included in each of the plurality of different digital sequences.

The plurality of digital sequences may include a first digital sequence generated from a first read-out sequence representing a magnitude of the neuron resonance signal acquired at each read-out time point of the magnetic resonance signal according to a first repetition period and a second digital sequence generated from a second read-out sequence representing a magnitude of the neuron resonance signal acquired at each read-out time point of the magnetic resonance signal according to a second repetition period different from the first repetition period.

The first digital sequence may be a sequence generated by padding first dummy data to the first read-out sequence to make the sampling period be a predetermined period, and the second digital sequence may be a sequence generated by padding second dummy data to the second read-out sequence such that the sampling period is the predetermined period.

The calculating may include calculating the correlation by superpositioning the first frequency spectrum of the first digital sequence and the second frequency spectrum of the second digital sequence.

The calculating may include convoluting the first digital sequence and the second digital sequence, transforming the convoluted digital sequence into a frequency band, and calculating the correlation from a frequency spectrum of the convoluted digital sequence.

The predetermined period may be equal to or smaller than a difference value between the first repetition period and the second repetition period.

According to another aspect of the present invention, a magnetic resonance imaging (MRI) signal processing apparatus includes: an input unit receiving a magnetic resonance signal of a neuron resonance signal; and a controller acquiring a plurality of different digital sequences respectively corresponding to a plurality of different repetition periods by sampling a magnetic resonance signal of a neuron resonance signal according to each of the plurality of different repetition periods, wherein the controller calculates correlation between the plurality of different digital sequences in a frequency band based on the plurality of different digital sequences.

According to another aspect of the present invention, a non-transitory computer-readable medium storing a program for executing a method of detecting a neuron resonance signal records a program executing: acquiring a plurality of different digital sequences respectively corresponding to a plurality of different repetition periods by sampling a magnetic resonance signal of a neuron resonance signal according to each of the plurality of different repetition periods; and calculating correlation between the plurality of different digital sequences in a frequency band based on the plurality of different digital sequences.

As described above, according to various exemplary embodiments of the present invention, the technique of processing data of a neuron resonance MRI by measuring a magnitude of a neuron resonance signal using a plurality of repetition times (or repetition periods) may be provided.

Also, the present invention may provide the technique of identifying a frequency component of a neuron resonance signal based on sampling data of a magnetic resonance signal of a neuron resonance signal according to a plurality of repetition times (or repetition periods) even in a state in which a neuron resonance signal cannot be predicted.

BRIEF DESCRIPTION OF THE DRAWING FIGURES

The above and/or other aspects of the present invention will be more apparent by describing certain exemplary embodiments of the present invention with reference to the accompanying drawings, in which.

DETAILED DESCRIPTION OF THE EXEMPLARY EMBODIMENTS

Figure 1:
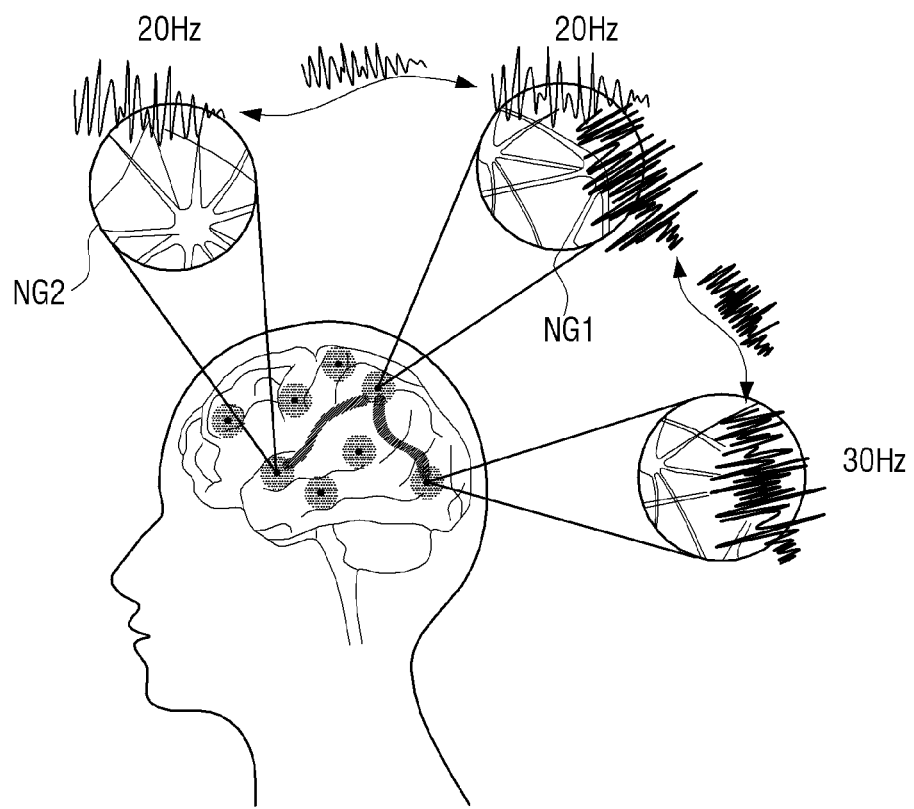
FIG. 1 is a diagram illustrating frequency-selective communication between brain regions in a neuron resonance MRI according to an exemplary embodiment of the present invention.

The exemplary embodiments of the present invention may be diversely modified. Accordingly, specific exemplary embodiments are illustrated in the drawings and are described in detail in the detailed description. The matters defined in the description, such as detailed construction and elements, are provided to assist in a comprehensive understanding of the invention. Thus, it is apparent that the exemplary embodiments of the present invention may be carried out without those specifically defined matters. Also, well-known functions or constructions are not described in detail since they would obscure the invention with unnecessary detail.

The terms "first", "second", etc. may be used to describe diverse components, but the components are not limited by the terms. The terms are only used to distinguish one component from the others.

The terms used in the present application are only used to describe the exemplary embodiments but are not intended to limit the scope of the invention. The singular expression also includes the plural meaning as long as it does not differently mean in the context. In the present application, the terms "include" and "consist of" designates the presence of features, numbers, steps, operations, components, elements, or a combination thereof that are written in the specification but does not exclude the presence or possibility of addition of one or more other features, numbers, steps, operations, components, elements, or a combination thereof. It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

In the exemplary embodiment of the present invention, a "module" or a "unit" performs at least one function or operation, and may be implemented with hardware, software, or a combination of hardware and software. In addition, a plurality of "modules" or a plurality of "units" may be integrated into at least one module except for a "module" or a "unit" which has to be implemented with specific hardware and may be implemented with at least one controller. As used herein, the singular forms "a,", "an" and "the" are intended to include the plural forms as well, unless the context clearly indicates otherwise.

The exemplary embodiments of the present invention will now be described in greater detail with reference to the accompanying drawings. In the following description, same drawing reference numerals are used for the same elements even in different drawings. Thus, description of the same elements is not repeated.

FIG. 1 is a diagram illustrating frequency-selective communication between brain regions in a neuron resonance magnetic resonance imaging (MRI) according to an exemplary embodiment of the present invention.

The brain of mammals exhibits resonance within a group of neurons by the interaction between neurons. As illustrated in FIG. 1, one neuron group NG1 resonates according to a specific frequency and selectively communicates with another neuron group NG2 that resonates at the same frequency.

The present invention provides a neuron resonance magnetic resonance imaging (NR-MRI) capable of measuring frequency-selective communication signals between brain regions. The present invention also provides a method of extracting a resonance frequency component inherent to neurons to provide an NR-MRI.

A resonance frequency component inherent to neurons may be identified by sampling a magnetic resonance signal of a neuron resonance signal and using the sampled magnetic resonance signal. That is, the magnetic resonance signal may be the same signal as the neuron resonance signal. A frequency of the neuron resonance signal is higher than a frequency at which the neuron resonance signal can be sampled by the present technology. For example, the frequency at which the neuron resonance signal can be sampled is 5 Hz or less, but the frequency of the neuron resonance signal is about tens of Hz. According to the Nyquist Theorem, data must be sampled based on a frequency at least twice a highest frequency of an input signal to restore the original analog signal without loss. However, as described above, since the frequency that can be sampled is lower than the frequency of the neuron resonance signal, the resonance frequency component inherent to neurons may not be identified only by the general sampling method. Thus, Korean Patent Registration No. 10-1683217 discloses a method of extracting a resonance frequency of neurons by assuming a resonance frequency of neurons as a specific value. However, since the resonance frequency of neurons differs according to brain regions, the aforementioned method may extract the resonance frequency of neurons in a specific region but has limitations in extracting the resonance frequency of neurons included in all brain regions. Thus, the present invention provides a general method of extracting the resonance frequency of neurons for all brain regions.

Figure 2:
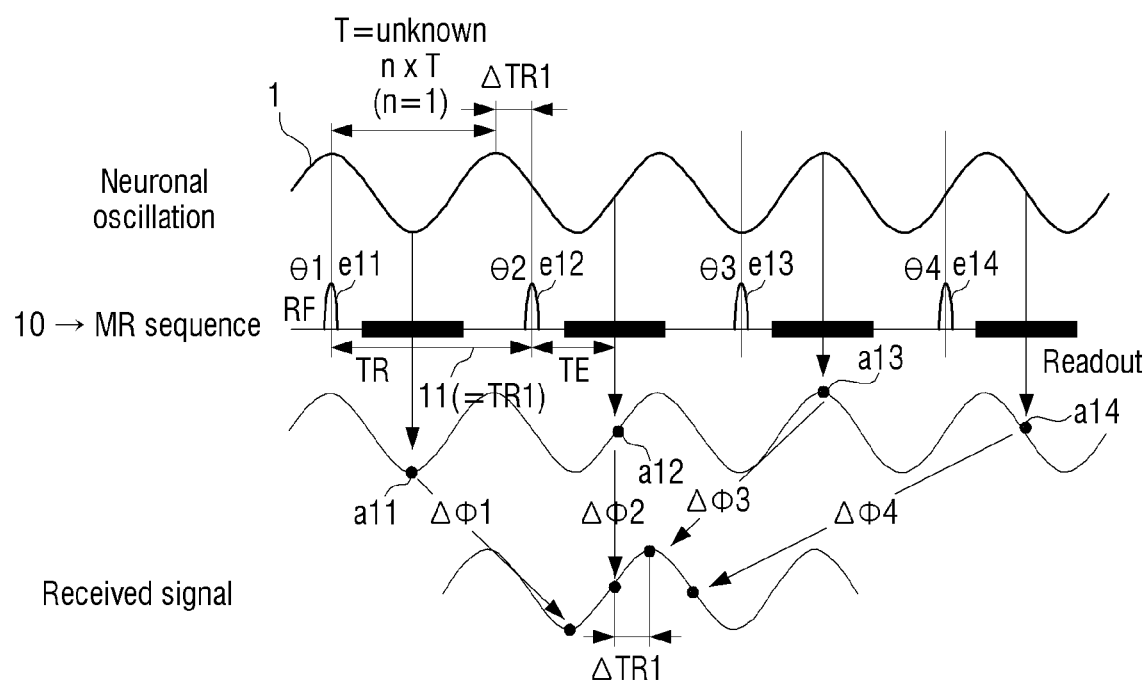
FIG. 2 is a diagram illustrating a process of acquiring a first digital sequence according to an exemplary embodiment of the present invention.

FIG. 2 is a diagram illustrating a process of acquiring a first digital sequence according to an exemplary embodiment of the present invention.

Figure 3:
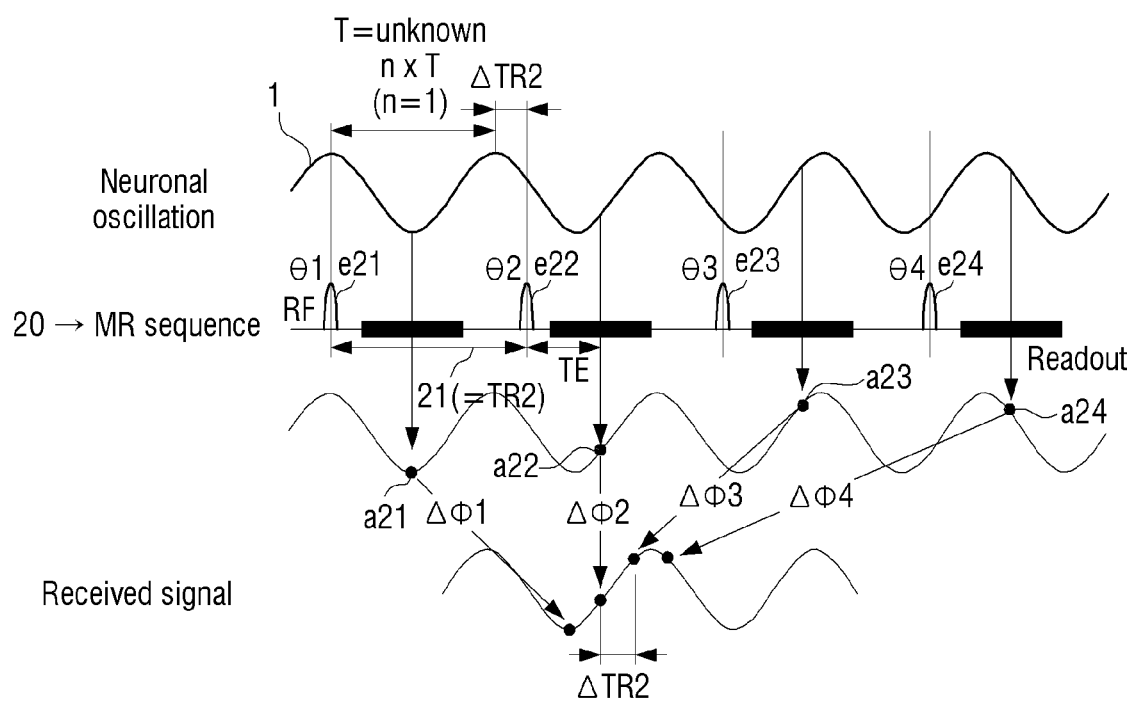
FIG. 3 is a diagram illustrating a process of acquiring a second digital sequence according to an exemplary embodiment of the present invention.

FIG. 3 is a diagram illustrating a process of acquiring a second digital sequence according to an exemplary embodiment of the present invention.

Hereinafter, a method of acquiring a frequency component of a neuron resonance signal according to an exemplary embodiment of the present invention will be described with reference to FIGS. 2 and 3.

Referring to FIG. 2, an MRI controller according to an exemplary embodiment of the present invention may control an MRI scanner to generate a first MRI sequence 10 having a first time to repetition (TR) 11. TR is a repetition time or repetition period at which a magnetic resonance signal of neuron resonance signal is sampled at regular intervals. The first MRI sequence 10 may include a plurality of periodically generated RF excitation signals e11, e12, e13, e14, . . . . The MRI controller may be a computing device integrally installed in the MRI scanner or a computing device provided separately from the MRI scanner.

Thereafter, the MRI controller may acquire first observation values a11, a12, a13, a14, . . . regarding a magnitude of the neuron resonance signal 1 of neurons to be observed at time points t11, t12, t13, and t14, which have elapsed by a predetermined value from time points at which the respective RF excitation signals e11, e12, e13, and e14, . . . were generated.

The time points (t11, t12, t13, and t14, . . . ) that have elapsed by a predetermined value may be referred to as read-out time points in this disclosure. Here, the predetermined value may correspond to a time echo (TE).

Discrete data formed by sequentially arranging the first observation values a11, a12, a13, a14, . . . acquired regarding the magnitude of the neuron resonance signal 1 may be referred to as a "first read-out sequence d11". For example, the first read-out sequence d11 may be given as d11=[a11, a12, a13, a14, . . . ]. A process of acquiring the first read-out sequence d11 may be referred to as a first process P1 in this disclosure hereinafter. A first digital sequence may be generated by padding dummy data to the acquired first read-out sequence d11, and if the acquired first read-out sequence d11 is not padded with the dummy data, the first read-out sequence d11 may be a first digital sequence.

Referring to FIG. 3, the MRI controller according to an exemplary embodiment of the present invention may control the MRI scanner to generate a second MRI sequence 20 having a second TR 21. The second MRI sequence 20 may include a plurality of RF excitation signals e21, e22, e23, e24, . . . which are periodically generated.

Here, the second TR 21 may be a value different from the first TR 11. For example, if the first TR 11 is repeated at 20 Hz, the second TR 21 may be repeated at 21 Hz. However, these specific numerical values are merely an example, and the TRs may be set to various values.

Thereafter, the MRI controller may acquire second observation values a21, a22, a23, a24, . . . regarding a magnitude of the neuron resonance signal 1 of neurons to be observed at time points t21, t22, t23, and t24, which have elapsed by a predetermined value from time points at which the respective RF excitation signals e21, e22, e23, and e24, . . . were generated.

Discrete data formed by sequentially arranging the second observation values a21, a22, a23, a24, . . . acquired regarding the magnitude of the neuron resonance signal 1 may be referred to as a "second read-out sequence d21". For example, the second read-out sequence d21 may be given as d21=[a21, a22, a23, a24, . . . ]. A process of acquiring the second read-out sequence d21 may be referred to as a second process P2 in this disclosure hereinafter. A second digital sequence may be generated by padding dummy data to the acquired second read-out sequence d21, and if the acquired second read-out sequence d21 is not padded with the dummy data, the second read-out sequence d21 may be a second digital sequence.

In FIG. 2 and FIG. 3, the neuron resonance signal 1 may have a period T. However, the period T is a value which is not known in advance, and the present invention relates to a technique of identifying the period T. The period T may be identified according to the exemplary embodiments of the present invention described hereinafter.

Meanwhile, FIGS. 2 and 3 illustrate a process of sampling a magnetic resonance signal of a neuron resonance signal based on two TRs (repetition period or repetition time). However, the magnetic resonance signal of the neuron resonance signal may be sampled based on two or more TRs to generate two or more digital sequences.

Figure 4:
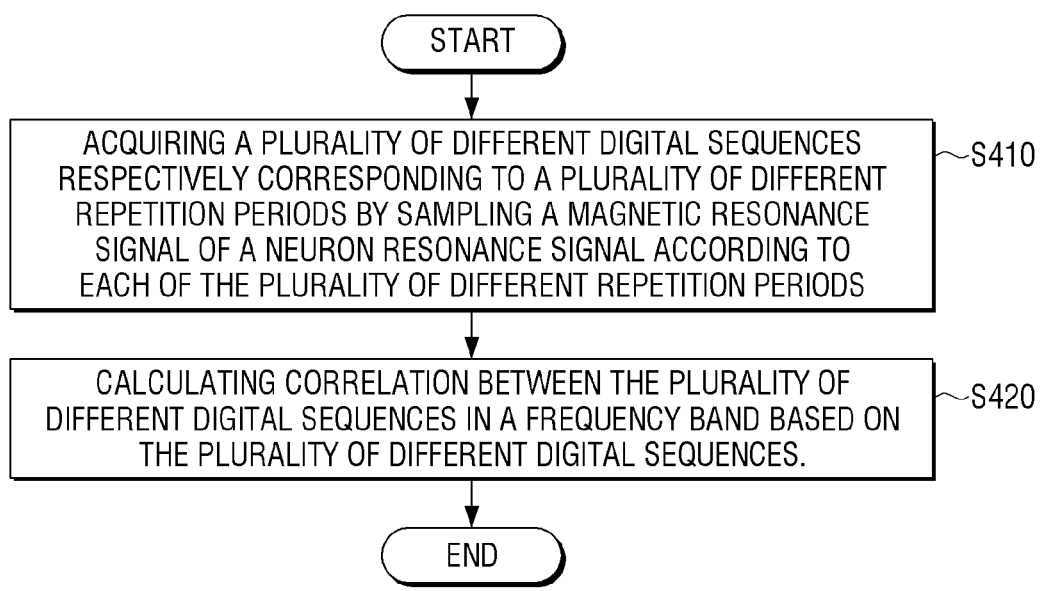
FIG. 4 is a flowchart illustrating a method of detecting a neuron resonance signal according to an exemplary embodiment of the present invention.

FIG. 4 is a flowchart illustrating a method of analyzing a neuron resonance signal according to an exemplary embodiment of the present invention.

Referring to FIG. 4, the MRI signal processing apparatus acquires a plurality of different digital sequences respectively corresponding to a plurality of different repetition periods by sampling a magnetic resonance signal of a neuron resonance signal according to each of the plurality of different repetition periods (S410). As described above, the plurality of different repetition periods include the first TR and the second TR. According to circumstances, the plurality of different repetition periods may include third to n-th TRs. Also, the MRI signal processing apparatus may acquire first to n-th digital sequence respectively corresponding to the TRs.

Based on the plurality of different digital sequences, the MRI signal processing apparatus calculates correlation between the plurality of different digital sequences in a frequency band (S420). For example, the MRI signal processing apparatus may transform each of the plurality of different digital sequences into a frequency band and superposition the plurality of different digital sequences of the transformed frequency bands to calculate correlation. Alternatively, the MRI signal processing apparatus may convolute the plurality of different digital sequences and transform the convoluted digital sequences into frequency bands to calculate correlation.

The MRI signal processing apparatus may set a certain resonance frequency of the neuron resonance signal and calculate correlation based on phase differences between the set certain resonance frequency and each of the different repetition periods and data of the plurality of acquired different digital sequences. In an exemplary embodiment, in case where the resonance frequency $f_{NO}$ of the neuron resonance signal is assumed to be 20 Hz, the period TNO is 50 ms. If the first TR is 60 ms, data sampled consecutively according to the first TR is data at the moments of $T_{NO}$+10 ms, $T_{NO}$+20 ms, $T_{NO}$+30 ms, . . . , $T_{NO}$+(10×n)ms. If the second TR is 50 ms, the data continuously sampled according to the second TR is data at the moments of $T_{NO}$-10 ms, $T_{NO}$-20 ms, $T_{NO}$-30 ms, . . . , $T_{NO}$-(10×n)ms. If the assumed resonance frequency of the neuron resonance signal matches a resonance frequency of an actual neuron resonance signal, energy in the frequency band of the data sampled according to the first TR and the second TR may be calculated to be larger than energy in the other bands. A specific process of calculating correlation between the plurality of different digital sequences by the MRI signal processing apparatus will be described hereinafter.

Meanwhile, the MRI signal processing apparatus may identify a frequency component in which a magnitude of calculated correlation is greater than a predetermined magnitude, as a frequency component of the neuron resonance signal.

Figure 5:
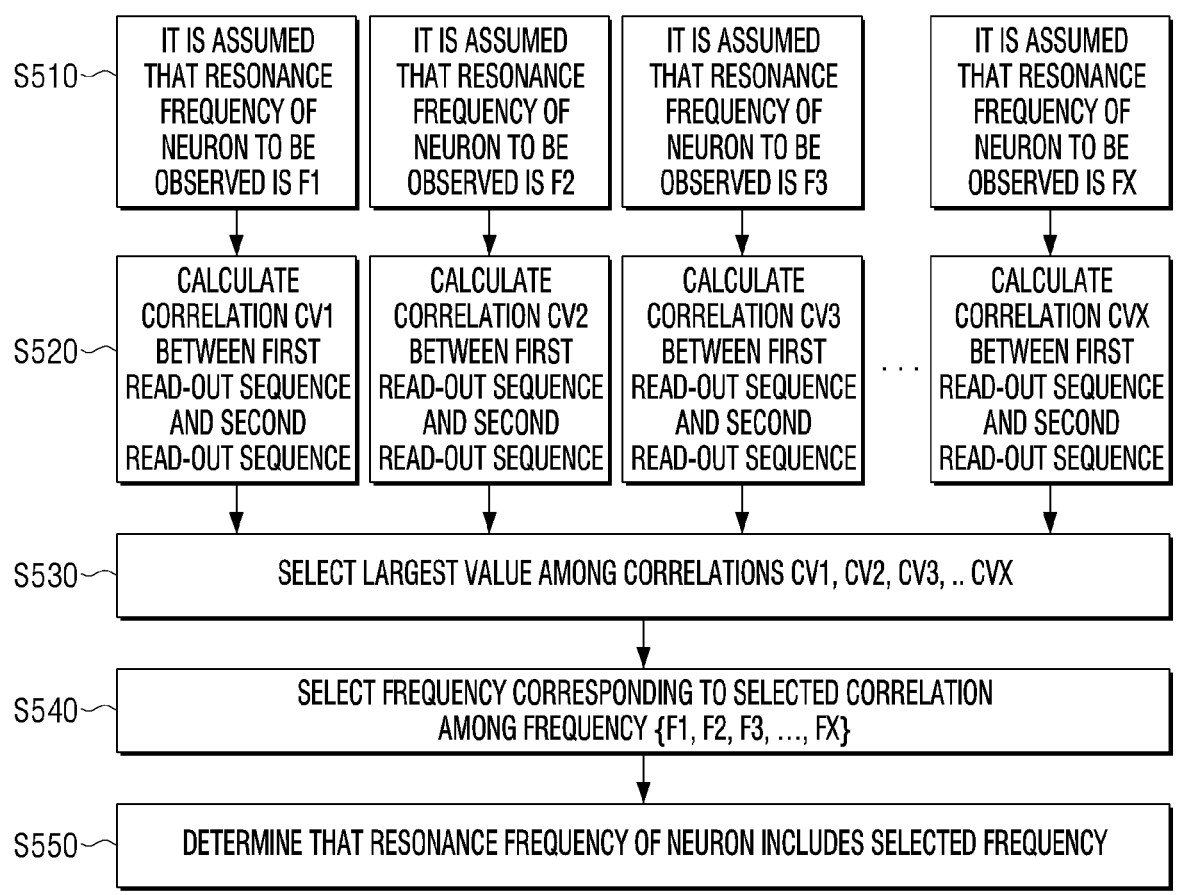
FIG. 5 is a diagram illustrating a method of detecting a frequency component of a neuron resonance signal using a first digital sequence and a second digital sequence according to an exemplary embodiment of the present invention.

FIG. 5 is a diagram illustrating a method of analyzing a frequency component of a neuron resonance signal using a first digital sequence and a second digital sequence according to an exemplary embodiment of the present invention. As described above, the read-out sequence may be referred to as a digital sequence and the analysis of the frequency component of the neuron resonance signal may use a plurality of digital sequences as the first to n-th digital sequences.

After it is assumed that a signal of neurons to be observed in the frequency component analysis method illustrated in FIG. 5 resonates in a specific assumed resonance frequency, a correlation calculation process PC of calculating correlation between the acquired first read-out sequence d11 and second read-out sequence d21 may be performed.

The correlation calculation process PC may be performed a plurality of times and the value of the assumed resonance frequency may be changed each time the correlation calculation process PC is performed. When the value of the assumed resonance frequency is changed, correlation between the first read-out sequence d11 and the second read-out sequence d21 may also be changed. Here, the changed assumed resonance frequency values may be expressed, for example, as f1, f2, f3, f4, . . . . The assumed resonance frequency values may refer to a plurality of different TRs (repetition times or repetition periods).

The present invention is provided for a situation in which the actual resonance frequency fr of the signal of the neuron is not known in advance. Therefore, which of the assumed resonance frequency values f1, f2, f3, f4, . . . . the actual resonance frequency fr is equal to or closest to may be detected according to exemplary embodiments of the present invention described hereinafter.

Referring to FIG. 5, a method of analyzing a frequency component of a neuron resonance signal according to an exemplary embodiment of the present invention may include the following steps.

In step S510, it is assumed that the resonance frequency of the neurons to be observed is a specific assumed resonance frequency fk (k=1, 2, 3, . . . , or x).

Under the assumption in step S510, correlation CVk between the first read-out sequence d11 and the second read-out sequence d21 described above is acquired in step S520.

The above-described steps S510 and S520 may be repeatedly performed, while changing the specific assumed resonance frequency fk to different values f1, f2, f3, . . . , fx. As a result, a set of correlations {CV1, CV2, CV3, . . . CVx} may be calculated.

In step S530, a largest value among the set of correlations {CV1, CV2, CV3, . . . CVx} may be selected.

In step S540, an assumed resonance frequency corresponding to the correlation selected from among the assumed resonance frequency values {f1, f2, f3, . . . , fx}.

In step S550, it may be determined that the selected assumed resonance frequency is included in the resonance frequency of the neuron.

Figure 6:
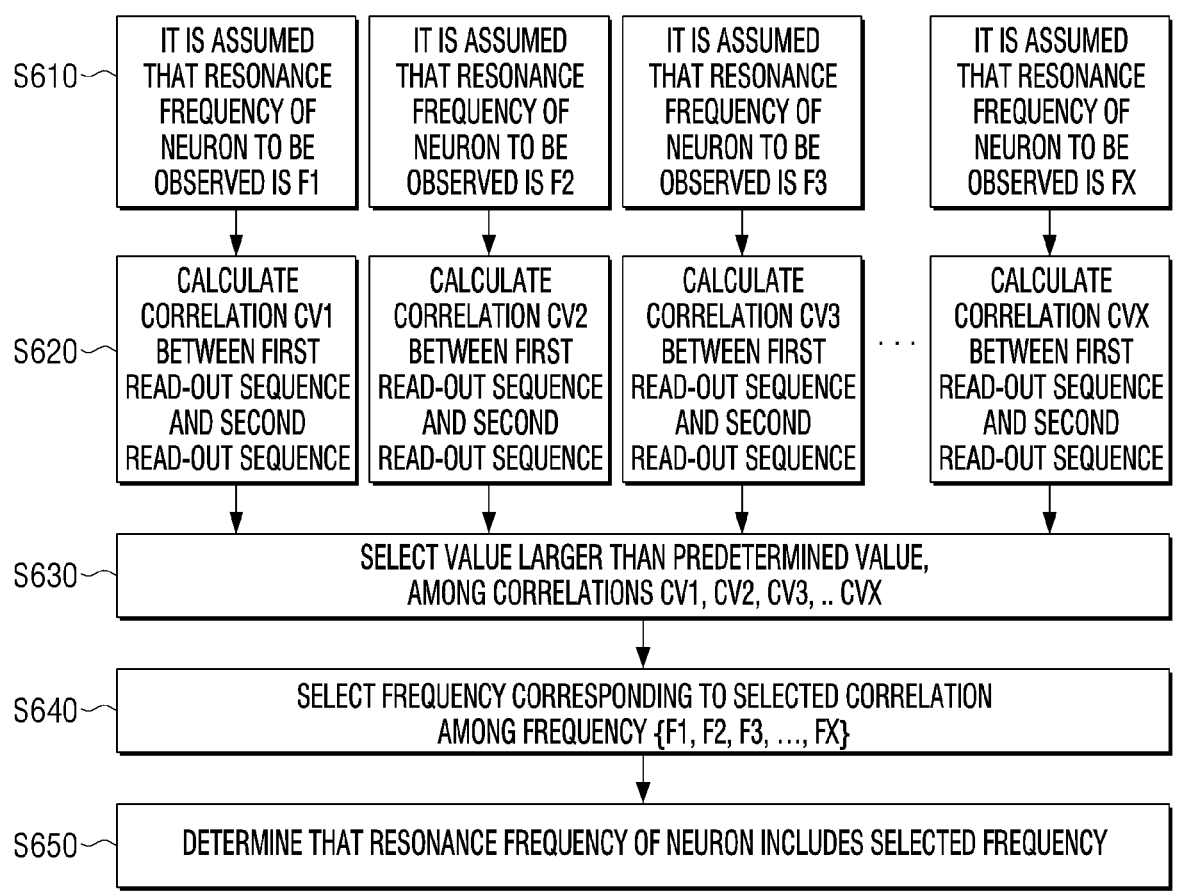
FIG. 6 is a diagram illustrating a method of detecting a frequency component of a neuron resonance signal using a first digital sequence and a second digital sequence according to another exemplary embodiment of the present invention.

FIG. 6 is a diagram illustrating a method of analyzing a frequency component of a neuron resonance signal using a first digital sequence and a second digital sequence according to another exemplary embodiment of the present invention. Referring to FIG.

Referring to FIG. 6, the method of analyzing a frequency component of a neuron resonance signal according to another exemplary embodiment of the present invention may include the following steps. Steps S610, S620, S640, and S650 may be the same as steps S510, S520, S540, and S550, respectively. Hereinafter, only differences from the method illustrated in FIG. 5 will be described.

In step S530, values larger than a predetermined value may be selected from among the set of correlations {CV1, CV2, CV3, . . . CVx}.

The first read-out sequence and the second read-out sequence may be acquired a plurality of times by performing the first process and the second process described above a plurality of times, respectively. Here, the SNR may be increased using the plurality of first read-out sequences and the plurality of second read-out sequences in the process of acquiring the correlation CVk. In FIGS. 5 and 6, it is described on the assumption that correlation between the first read-out sequence d11 and the second read-out sequence d21 can be calculated. Hereinafter, a specific method of calculating correlation will be described. According to an exemplary embodiment of the present invention, correlation may be calculated in a frequency region.

According to an exemplary embodiment of the present invention, the method of calculating correlation between the first read-out sequence d11 and the second read-out sequence d21 may use a frequency spectrum correlation calculation process P3.

Figure 7:
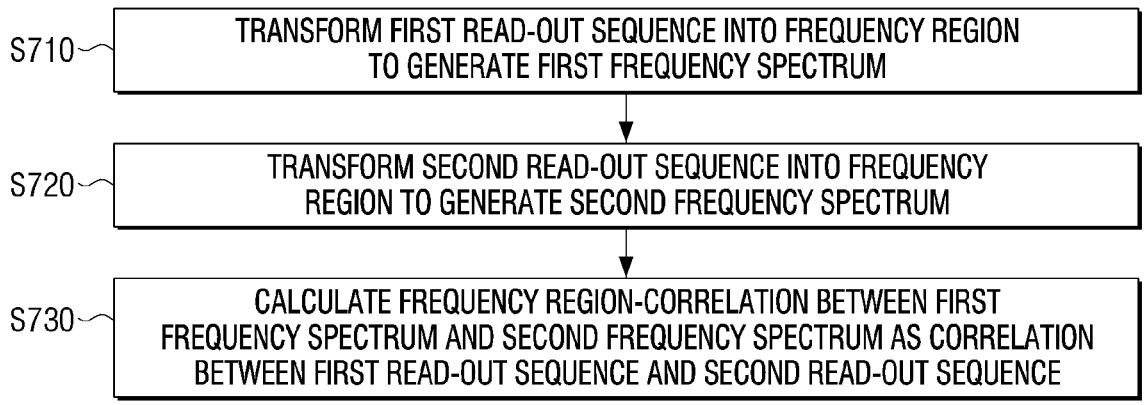
FIG. 7 is a flowchart illustrating a process of calculating a frequency spectrum correlation provided according to an exemplary embodiment of the present invention.

FIG. 7 is a flowchart illustrating a frequency spectrum correlation calculation process according to an exemplary embodiment of the present invention.

The frequency spectrum correlation calculation process P3 may be performed on the assumption that neurons to be observed resonates at a specific assumed resonance frequency.

The frequency spectrum correlation calculating process P3 may include:

Step S710: transforming the first read-out sequence into a frequency region to generate a first frequency spectrum f11, [94] Step S720: transforming the second read-out sequence into a frequency region to generate a second frequency spectrum f21, and [95] Step S730: calculating frequency region-correlation between the first frequency spectrum and the second frequency spectrum as correlation between the first read-out sequence and the second read-out sequence.

Here, the method of calculating correlation between the first read-out sequence d11 and the second read-out sequence d21 may include performing the frequency spectrum correlation calculation process P3 one or more times, while changing the specific assumed resonance frequency. For example, the frequency spectrum correlation calculation process P3 may be performed on each frequency included in the predetermined assumed resonance frequency set {f1, f2, f3, . . . , fx}, and, as a result, a plurality of frequency region-correlations may be calculated.

Figure 8:
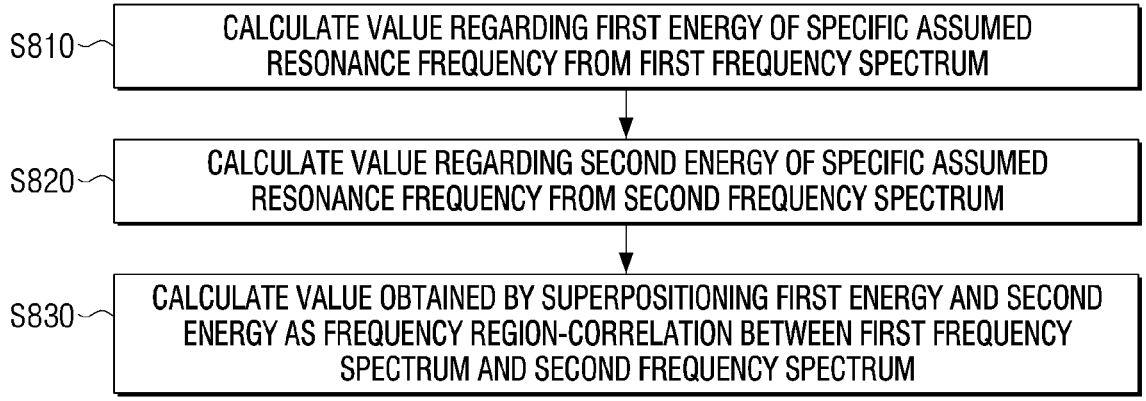
FIG. 8 is a flowchart illustrating a method of calculating a frequency region correlation between a first frequency spectrum and a second frequency spectrum according to an exemplary embodiment of the present invention.

The frequency component analysis method of analyzing the frequency component of the neuron resonance signal illustrated in FIGS. 5 and 6 may include detecting a frequency component of a neuron resonance signal based on one or more frequency region-correlations acquired for one or more specific assumed resonance frequencies. [98] Here, the frequency region-correlation between the first frequency spectrum and the second frequency spectrum included in step S730 may be calculated using steps S810 to S830 illustrated in the flowchart of FIG. 8, for example. Here, it is assumed that the neurons to be observed resonate at a specific assumed resonance frequency.

FIG. 8 is a flowchart illustrating a method of calculating a frequency region correlation between a first frequency spectrum and a second frequency spectrum according to an exemplary embodiment of the present invention.

In step S810, a value related to first energy of a specific assumed resonance frequency may be calculated in the first frequency spectrum.

In step S820, a value related to the second energy of the specific assumed resonance frequency may be calculated in the second frequency spectrum.

In step S830, a value acquired by superpositioning the first energy and the second energy may be calculated as a frequency region-correlation between the first frequency spectrum and the second frequency spectrum.

Here, the 'superpositioning' in step S830 may be a process of reinforcing the first energy using the second energy, and reinforcing the first energy using the second energy may refer to calculation of combining the first energy and the second energy using a method of adding, multiplying, or the like, the first energy and the second energy. Here, the first read-out sequence may be acquired by sampling the neuron resonance signal at the first TR interval. The neuron resonance signal is assumed to resonate at a specific assumed resonance frequency. Also, the second read-out sequence may be acquired by sampling the neuron resonance signal at the second TR interval. The neuron resonance signal is assumed to resonate at a specific assumed resonance frequency.

A person skilled in the art will understand that, when it is assumed that neurons to be observed resonate at a specific assumed resonance frequency, a first maximum frequency represented by the first frequency spectrum and a second maximum frequency represented by the second frequency spectrum may be varied according to sampled data based on each specific assumed resonance frequency value and the first TR or the second TR.

For example, when it is assumed that the neuron resonance signal resonates at 50 Hz, the period of the neuron resonance signal is 20 ms.

Here, when the first TR is 90 ms, a phase of the neuron resonance signal observed at each read-out time point is shifted by 10 ms, and here, the first maximum frequency of the first frequency spectrum is 1000/10 ms=100 Hz.

When the second TR is 91 ms, the phase of the neuron resonance signal observed at each read-out time point is shifted by 9 ms, and the second maximum frequency of the second frequency spectrum is 1000/9 ms=~111 Hz.

When the first maximum frequency and the second maximum frequency are determined as described above, the value related to the first energy corresponding to 50 Hz, the specific assumed resonance frequency, may be found from the first frequency spectrum, and the value related to the second energy corresponding to 50 Hz, the specific assumed resonance frequency, may be found from the second frequency spectrum as presented in steps S810 and S820.

Thereafter, as presented in step S830, the value acquired by superpositioning the first energy and the second energy may be calculated as a frequency region-correlation between the first frequency spectrum and the second frequency spectrum.

Meanwhile, a first case where the specific assumed resonance frequency is the same as the actual resonance frequency at which the observed neurons resonate, and a second case where the specific assumed resonance frequency is not the same as the actual resonance frequency may be classified. For example, when actual resonance frequency of neurons is 50 Hz, a first case where the specific assumed resonance frequency is assumed to be 50 Hz and a second case were the specific assumed resonance frequency is 55 Hz may be classified.

Here, the frequency region-correlation calculated in the first case may be larger than the frequency region-correlation calculated in the second case. Thus, it may be determined that the specific assumed resonance frequency 50 Hz is the actual resonance frequency in the first case which exhibits larger correlation.

Figure 9:
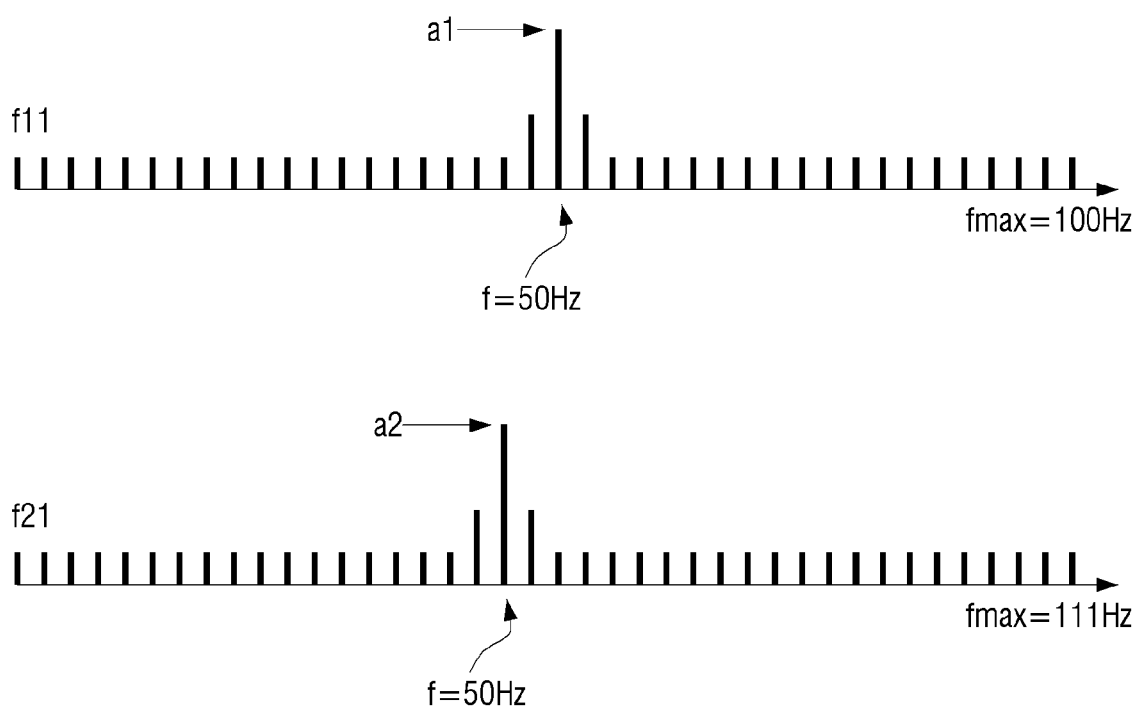
FIGS. 9 and 10 are diagrams illustrating a first frequency spectrum and a second frequency spectrum according to an exemplary embodiment of the present invention.
Figure 10:
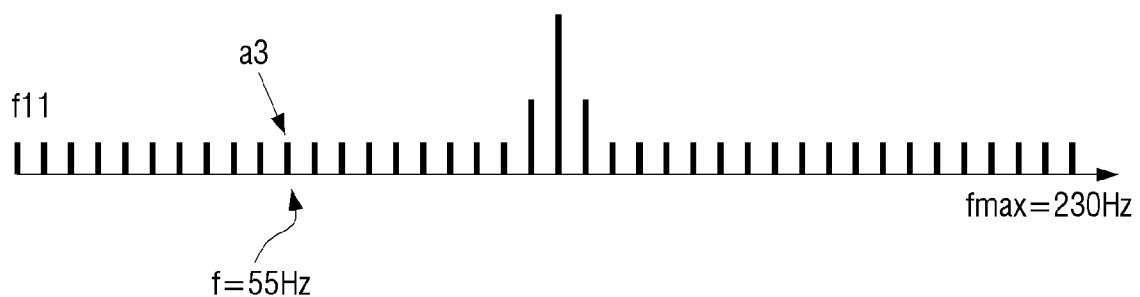
Figure 10:
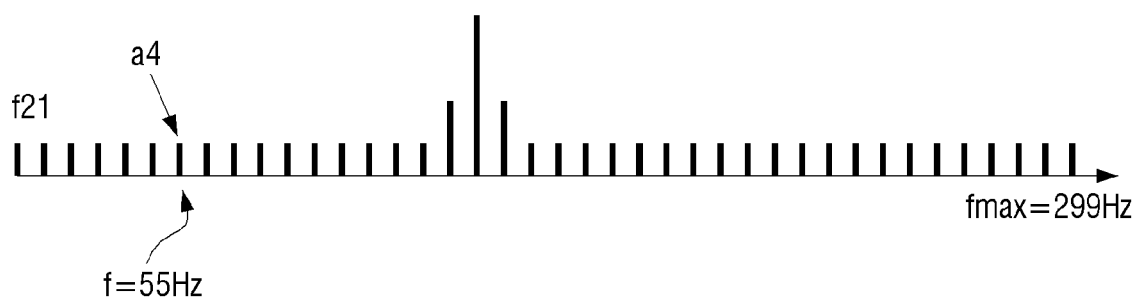

FIGS. 9 and 10 are diagrams illustrating a first frequency spectrum and a second frequency spectrum according to an exemplary embodiment of the present invention.

FIG. 9 shows a first frequency spectrum and a second frequency spectrum according to an exemplary embodiment of the present invention, that is, a frequency spectrum when an unknown resonance frequency of neurons is assumed to be a first value.

FIG. 9 is a diagram for explaining the first case, i.e., the case where the actual resonance frequency of neurons is the same as the assumed resonance frequency, in which a maximum frequency fmax of the first frequency spectrum f11 is 100 Hz and a maximum frequency fmax of the second frequency spectrum f21 is 111 Hz. The MRI signal processing apparatus may detect first energy a1 corresponding to the specific assumed resonance frequency 50 Hz in the first frequency spectrum and second energy a2 corresponding to the specific assumed resonance frequency 50 Hz in the second frequency spectrum and superposition the first energy and the second energy to calculate a first superposition value a1*a2.

FIG. 10 shows a first frequency spectrum and a second frequency spectrum derived according to an exemplary embodiment of the present invention, that is, a frequency spectrum when an unknown resonance frequency of neurons is assumed to be a second value different from the first value. The frequency spectra illustrated in FIG. 10 are the same as the frequency spectra illustrated in FIG. 9, but the scales of the frequency axes are different from each other.

In the second case of FIG. 10, that is, in case where the actual resonance frequency of neurons is different from the assumed resonance frequency, for example, the actual resonance frequency of neurons may be set to 50 Hz, the first TR may be set to 90 ms, the second TR may be set to 91 ms, and the specific assumed resonance frequency may be set to be 53 Hz. Here, a phase of the neuron resonance signal observed at every read-out time point of the first TR is shifted by 4.34 ms in each observation and the first maximum frequency of the first frequency spectrum is 1000/4.34 ms=230 Hz. Also, a phase of the neuron resonance signal observed at every read-out time point of the second TR is shifted by 3.34 ms in each observation and the second maximum frequency of the second frequency spectrum is 1000/3.34 ms=−299 Hz.

The MRI signal processing apparatus may detect first energy a3 corresponding to 55 Hz of the specific assumed resonance frequency in the first frequency spectrum and detects second energy a4 corresponding to 55 Hz of the specific assumed resonance frequency in the second frequency spectrum and superposition the first energy and the second energy to calculate a second superposition value a3*a4.

As illustrated in FIGS. 9 and 10, it can be seen that the first superposition value is larger than the second superposition value. That is, when the assumed resonance frequencies match, the energy values calculated in the frequency band are reinforced and larger values are calculated, and when the assumed resonance frequencies do not match, the energy values calculated in the frequency band are canceled out and a smaller value is calculated. Therefore, since 50 Hz assumed when the first superposition value having a larger value is calculated is the actual resonance frequency of neurons, so that the specific assumed resonance frequency 50 Hz may be determined as the actual resonance frequency of neurons. That is, the MRI signal processing apparatus may identify a frequency component whose magnitude of correlation is calculated to be greater than a predetermined magnitude, as a frequency component of the neuron resonance signal.

A method of determining a resonance frequency of neurons according to another exemplary embodiment of the present invention will be described with reference to FIGS. 11 and 12.

Figure 11:
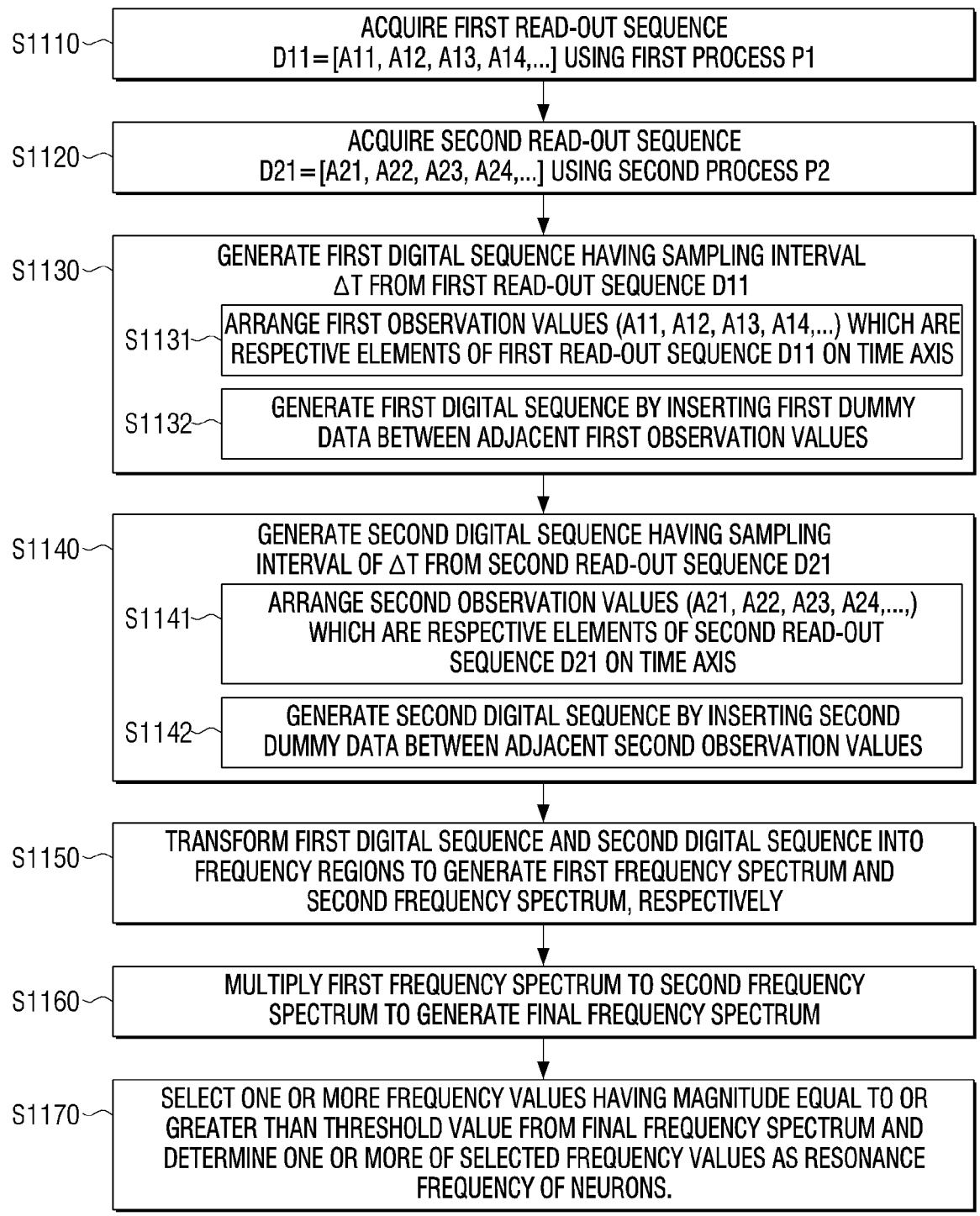
FIG. 11 is a flowchart illustrating a method of identifying a resonance frequency of neurons according to an exemplary embodiment of the present invention.

FIG. 11 is a flowchart illustrating a method of identifying a resonance frequency of neurons according to an exemplary embodiment of the present invention.

In step S1110, the first read-out sequence d11=[a11, a12, a13, a14, . . . ] may be acquired using the first process P1 described above.

In step S1120, the second read-out sequence d21=[a21, a22, a23, a24, . . . ] may be acquired using the second process P2 described above.

In step S1130, a first digital sequence having a sampling interval ΔT may be generated from the first read-out sequence d11=[a11, a12, a13, a14, . . . ]. Meanwhile, step S1130 may include the following steps.

In step S1131, first observation values a11, a12, a13, a14, . . . , which are respective elements of the first read-out sequence d11=[a11, a12, a13, a14, . . . ] may be arranged on the time axis. Here, a time interval between the first observation values adjacent to each other may be the same as the first TR 11.

In step S1132, a first digital sequence may be generated by inserting first dummy data between the adjacent first observation values. Here, the first dummy data may be '0' or a constant or may be values generated by interpolating first observation values arranged on a time axis. Here, a time interval of two elements adjacent to each other on the time axis, among the elements of the generated first digital sequence, may be set to ΔT. ΔT may be understood as a sampling interval.

In step S1140, a second digital sequence having a sampling interval of ΔT may be generated from the second read-out sequence d21=[a21, a22, a23, a24, . . . ]. Meanwhile, step S1140 may include the following steps.

In step S1141, the second observation values a21, a22, a23, a24, . . . , which are respective elements of the second read-out sequence d21=[a21, a22, a23, a24, . . . ] may be arranged on the time axis. Here, a time interval between the second observation values adjacent to each other may be the same as that of the second TR 21.

In step S1142, a second digital sequence may be generated by inserting second dummy data between the adjacent second observation values. Here, the second dummy data may be '0' or a constant or may be a value generated by interpolating the second observation values arranged on the time axis. Here, the time interval of two elements adjacent to each other on the time axis, among the elements of the generated second digital sequence, may be set to ΔT. ΔT may be understood as a sampling interval.

Here, the maximum value of ΔT may be abs(first TR(11)−second TR(21)).

In step S1150, the first digital sequence and the second digital sequence may be transformed into frequency regions to generate a first frequency spectrum and a second frequency spectrum, respectively. To this end, Fourier transform may be used. Here, the number of the first digital sequences used for the transform may be equal to the number of the second digital sequences used for the transform.

In step S1160, the first frequency spectrum may be multiplied to the second frequency spectrum to generate a final frequency spectrum. Multiplying may mean that two spectrum values corresponding to the same frequency magnitude in the first and second frequency spectra are multiplied together.

In step S1170, one or more frequency values having a magnitude equal to or greater than a threshold value may be selected from the final frequency spectrum, and one or more of the selected frequency values may be determined as a resonance frequency of neurons.

Figure 12:
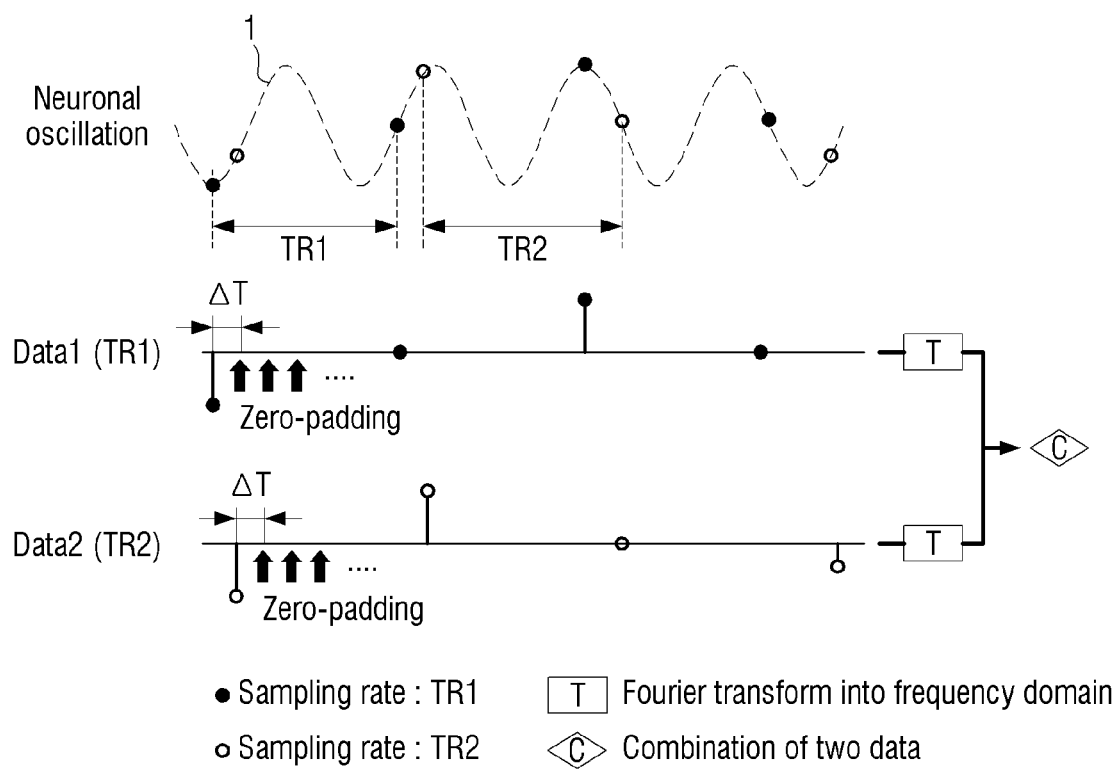
FIG. 12 is a diagram illustrating a method of identifying a resonance frequency of neurons according to an exemplary embodiment of the present invention.

FIG. 12 is a diagram illustrating a method of identifying a resonance frequency of neurons according to an exemplary embodiment of the present invention.

The first read-out sequence d11 sampled at the sampling rate TR1 on the time axis extending in the left and right direction of FIG. 12 may be transformed into data of the first digital sequence having the new sampling interval ΔT. Similarly, the second read-out sequence d21 sampled at the sampling rate TR2 may be transformed into data of the second digital sequence having the sampling interval ΔT.

Here, a non-sampled space may be filled with 0 or interpolation.

For example, in the case of TR1=90 ms and ΔT=1 ms, spaces between signal values acquired from the first read-out sequence d11 sampled at the sampling rate of TR1 may be filled with 89 dummy data '0'. The first frequency spectrum acquired by performing FFT on the first digital sequence acquired thusly may represent a frequency range of 0 to 500 Hz.

For example, in the case of TR2=91 ms, ΔT=1 ms, spaces between signal values acquired from the second read-out sequence d21 sampled at the sampling rate TR2 may be filled with 90 dummy data '0'. The second frequency spectrum acquired by performing FFT on the second digital sequence acquired thusly may represent a frequency range of 0 to 500 Hz.

Since the first digital sequence and the second digital sequence have more dummy data than the actually measured data, a large amount of aliased signals may appear in the calculated first frequency spectrum and second frequency spectrum. To suppress these aliased signals, the first frequency spectrum and the second frequency spectrum may be multiplied together to produce a final frequency spectrum. Accordingly, the frequency of neurons may be finally identified.

In the method of filling spaces between data with dummy data '0', the maximum value of ΔT may be the absolute value of TR1–TR2. That is, if TR1=90 ms, TR2=100 ms, ΔT may be a maximum of 10 ms, and in this case, spaces between the signals in the TR1 data may be filled with 8 dummy data '0' each and spaces between the signals in TR2 data may be filled with 9 dummy data '0' each. Thereafter, the ranges of the first frequency spectrum and the second frequency spectrum acquired after the Fourier transform may be all 0 to 50 Hz. Also, in this case, ΔT may be 1 ms. Here, preferably, ΔT is a divisor of 10 ms.

A method of analyzing a frequency component of a neuron resonance signal provided according to various exemplary embodiments of the present invention may include the following steps.

Descriptions will be given below with reference to FIGS. 2, 3, and 13.

Figure 13:
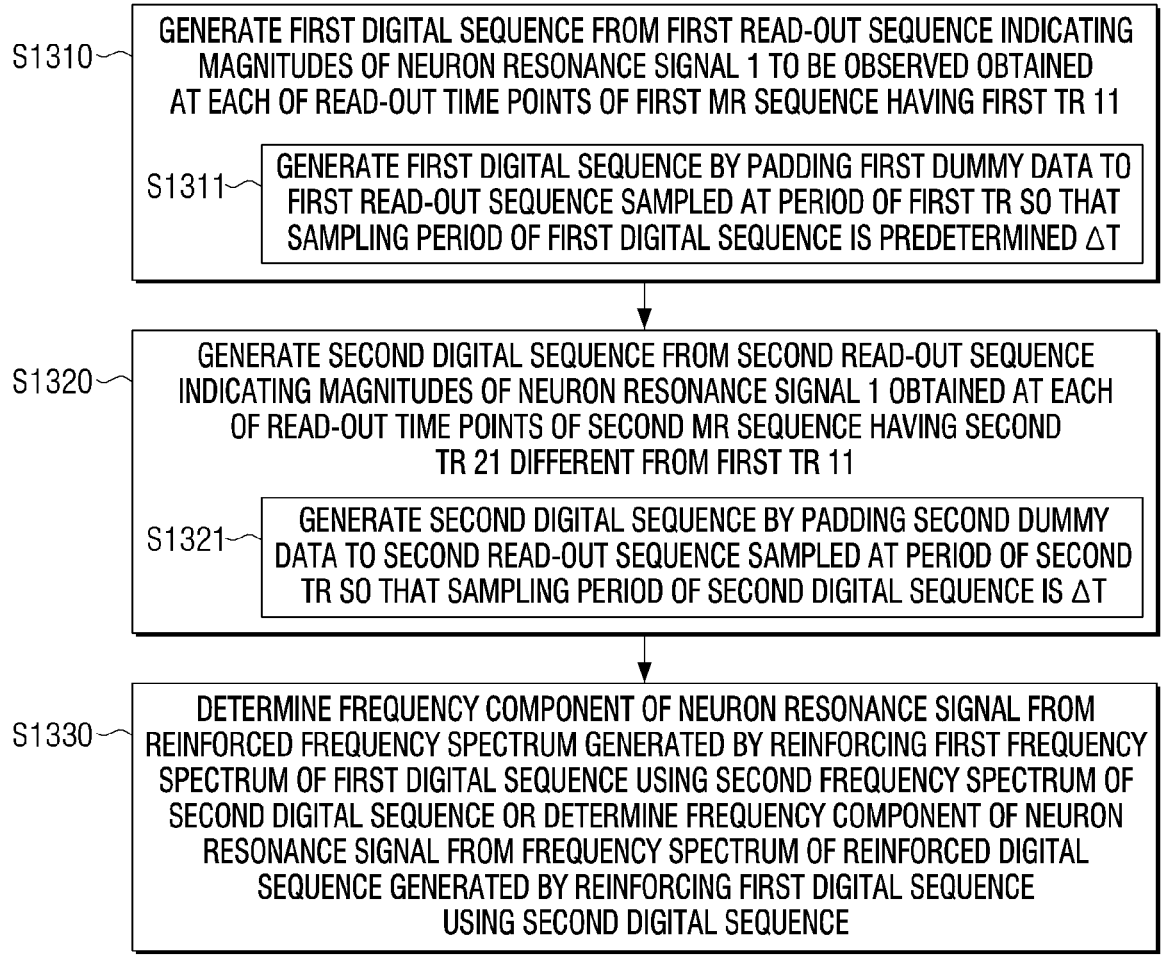
FIGS. 13 through 15 are flowcharts illustrating a method of identifying a resonance frequency of neurons according to various exemplary embodiments.

FIG. 13 is a flowchart illustrating a method of identifying a frequency component of a neuron resonance signal provided according to an exemplary embodiment of the present invention.

In step S1310, a first digital sequence may be generated from the first read-out sequence d11 indicating the magnitudes a101, a102, a03, a104, . . . of a neuron resonance signal 1 to be observed acquired at each of the read-out time points t11, t12, t13, . . . of the first MR sequence 10 having the first TR 11.

In step S1320, a second digital sequence may be generated from the second read-out sequence d21 indicating the magnitudes a201, a202, a203, a204, . . . of the resonance signal 1 acquired at each of the read-out time points t21, t22, t23, . . . of the second MR sequence 20 having the second TR 21 different from the first TR 11.

In operation S1330, a frequency component of the neuron resonance signal may be determined from a frequency spectrum generated by reinforcing the first frequency spectrum of the first digital sequence using the second frequency spectrum of the second digital sequence, or the frequency component of the neuron resonance signal may be identified from a frequency spectrum of a digital sequence generated by reinforcing the first digital sequence using the second digital sequence.

Here, step S1310 may include step S1311 of generating a first digital sequence by padding the first dummy data to the first read-out sequence so that the sampling period of the first digital sequence is the predetermined ΔT.

Step S1320 may include step S1321 of generating a second digital sequence by padding the second dummy data to the second read-out sequence so that the sampling period of the second digital sequence is ΔT.

Also, in step S1330, the frequency component of the neuron resonance signal may be identified from a reinforced frequency spectrum generated by reinforcing the first frequency spectrum of the first digital sequence using the second frequency spectrum of the second digital sequence. Here, the reinforcing may be an addition or multiplication operation.

Alternatively, in step S1330, the frequency component of the neuron resonance signal may be identified from the reinforced frequency spectrum generated by reinforcing the first digital sequence using the second digital sequence. Here, the reinforcing may be a convolution operation.

The predetermined sampling period ΔT may be less than or equal to an absolute value of a difference between the first TR and the second TR. The first dummy data may be a value '0', a constant, or a value interpolated from the first read-out sequence, and the second dummy data may be a value '0', a constant, or a value interpolated from the second read-out sequence.

A method of analyzing a frequency component of a neuron resonance signal provided according to another exemplary embodiment of the present invention may include the following steps.

Descriptions will be given below with reference to FIGS. 2, 3, 14, and 15.

Figure 14:
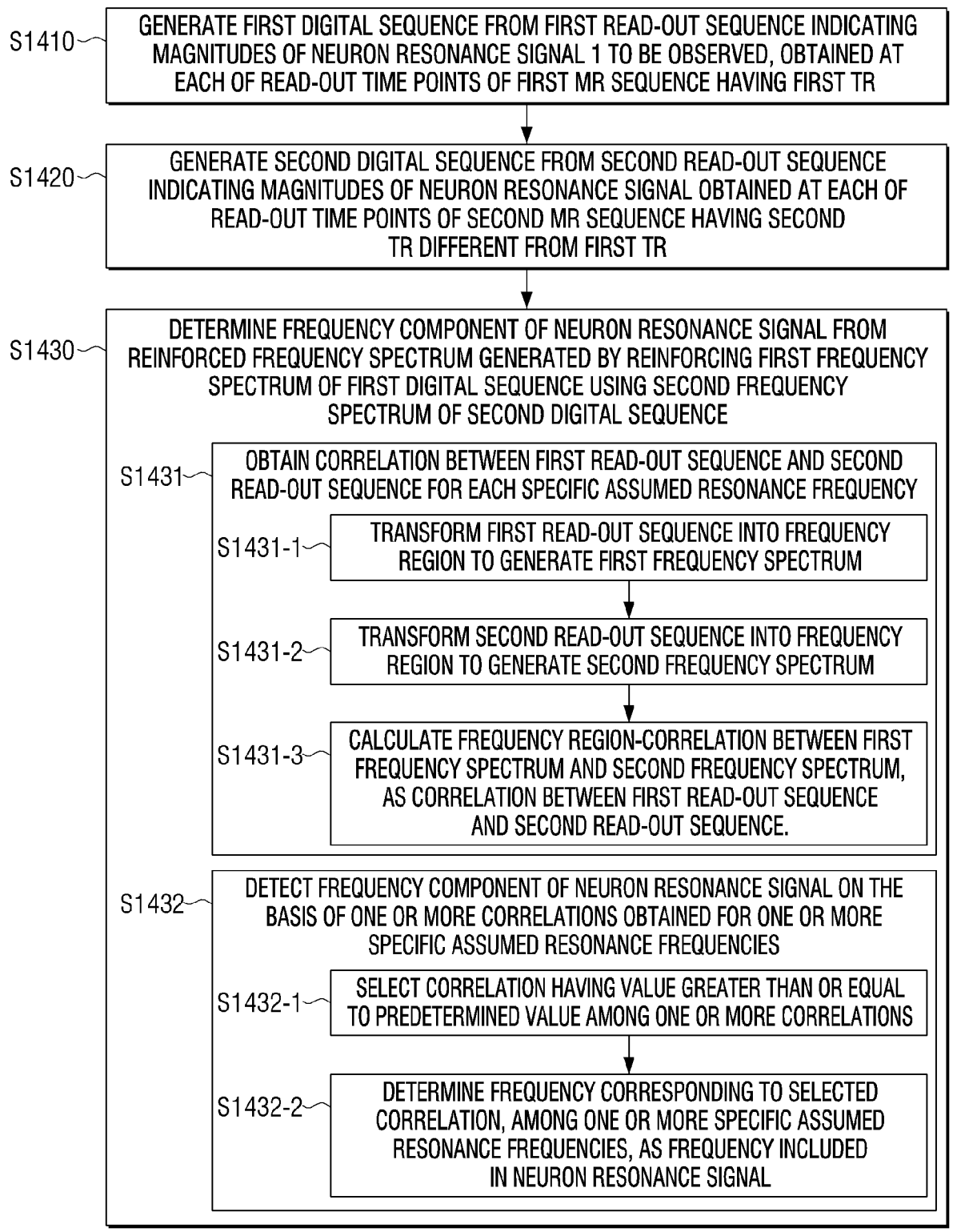

FIG. 14 is a flowchart illustrating a method of analyzing a frequency component of a neuron resonance signal provided according to another exemplary embodiment of the present invention.

In step S1410, the first digital sequence may be generated from the first read-out sequence d11 indicating the magnitudes a101, a102, a103, a104 of the neuron resonance signal 1 to be observed, acquired at each of the read-out time points t11, t12, t13, . . . of the first MR sequence 10 having the first TR 11.

In step S1420, the second digital sequence may be generated from the second read-out sequence d21 indicating the magnitudes a201, a202, a203, a204, . . . of the neuron resonance signal 1 acquired at each of the read-out time points t21, t22, t23, . . . of the second MR sequence 20 having the second TR 21 different from the first TR 11.

In step S1430, the frequency component of the neuron resonance signal may be identified from the frequency spectrum generated by reinforcing the first frequency spectrum of the first digital sequence using the second frequency spectrum of the second digital sequence.

Here, the first digital sequence may be a first read-out sequence, and the second digital sequence may be a second read-out sequence. In step S1430, the frequency component of the neuron resonance signal may be identified from the frequency spectrum generated by reinforcing the first frequency spectrum of the first digital sequence using the second frequency spectrum of the second digital sequence. Here, the reinforcing may be an addition or multiplication operation.

Step S1430 may further include the following steps.

In step S1431, assuming that the neurons to be observed resonate at one or more specific resonance frequencies, correlation between the first read-out sequence and the second read-out sequence for each specific assumed resonance frequency may be acquired.

In step S1432, the frequency component of the neuron resonance signal may be detected based on one or more correlations acquired for one or more specific assumed resonance frequencies. Step S1432 may include step of selecting correlation having a value greater than or equal to a predetermined value among the one or more correlations (S1432-1) and identifying a frequency corresponding to the selected correlation, among the one or more specific assumed resonance frequencies, as a frequency included in the neuron resonance signal (S1432-2).

Here, the MRI signal processing apparatus may acquire the first read-out sequence a plurality of times by performing S1410 step a plurality of times, acquire the second read-out sequence a plurality of times by performing step S1420 a plurality of times, and subsequently calculate correlation using the plurality of acquired first read-out sequences and the plurality of acquired second read-out sequences.

Here, in step S1431, the frequency spectrum correlation including the following steps may be calculated. In step S1431-1, when the neurons to be observed are assumed to resonate at a specific resonance frequency, the first read-out sequence may be transformed into a frequency region to generate the first frequency spectrum. In step S1431-2, when the neurons to be observed are assumed to resonate at a specific resonance frequency, the second read-out sequence may be transformed into a frequency region to generate the second frequency spectrum. In step S1431-3, the frequency region-correlation between the first frequency spectrum and the second frequency spectrum may be calculated as correlation between the first read-out sequence and the second read-out sequence. In step S1431, the frequency spectrum correlation calculation process may be performed one or more times, while changing the assumed resonance frequency.

Figure 15:
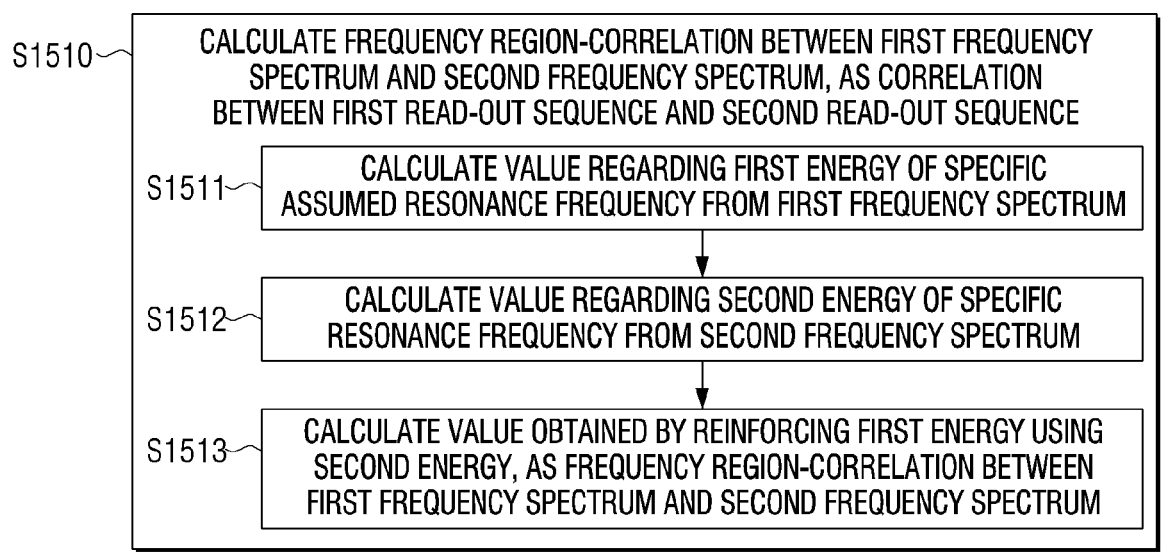

FIG. 15 is a flowchart illustrating a method of calculating a frequency region-correlation between a first frequency spectrum and a second frequency spectrum as correlation between a first read-out sequence and a second read-out sequence according to an exemplary embodiment of the present invention.

Step S1510 may include the following steps S1511, S1512, and S1513. Step In S1511, a value regarding first energy of a specific resonance frequency may be calculated from the first frequency spectrum. In step S1512, a value regarding second energy of the specific resonance frequency may be calculated from the second frequency spectrum. In step S1513, a value acquired by reinforcing the first energy using the second energy may be calculated as a frequency region-correlation between the first frequency spectrum and the second frequency spectrum. Here, reinforcing may refer to an addition or multiplication operation.

Referring back to FIG. 14, step S1432 may include detecting a frequency component of the neuron resonance signal based on one or more frequency region-correlations acquired for one or more specific resonance frequencies.

Various exemplary embodiments of the method of detecting a neuron resonance signal have been described so far. Hereinafter, an MRI signal processing apparatus for detecting a neuron resonance signal will be described.

Figure 16:
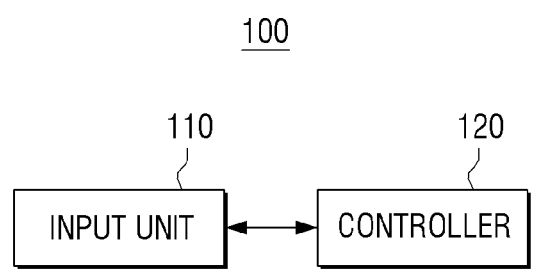
FIG. 16 is a block diagram of an MRI signal processing apparatus according to an exemplary embodiment of the present invention.

FIG. 16 is a block diagram of an MRI signal processing apparatus according to an exemplary embodiment of the present invention.

Referring to FIG. 16, the MRI signal processing apparatus 100 includes an input unit 110 and a controller 120. The input unit 110 receives a magnetic resonance signal of a neuron resonance signal.

The controller 120 samples the magnetic resonance signal of the neuron resonance signal according to each of a plurality of different repetition periods to acquire a plurality of different digital sequences respectively corresponding to the plurality of different repetition periods. The repetition period refers to a period for sampling the magnetic resonance signal of the neuron resonance signal at regular intervals and may also be expressed as a time to repetition (TR). The repetition period may include a first TR and a second TR, and may include a third TR, . . . , an n-th TR according to circumstances.

The controller 120 calculates correlation between a plurality of different digital sequences in a frequency band based on a plurality of different digital sequences. The controller 120 may identify a frequency component in which a magnitude of the calculated correlation is equal to or greater than a predetermined magnitude, as a frequency component of the neuron resonance signal.

Meanwhile, the controller 120 may transform each of the plurality of different digital sequences into a frequency band and may superposition the plurality of different digital sequences of the transformed frequency bands to calculate correlation. Alternatively, the controller 120 may convolute the plurality of different digital sequences and transform the convoluted digital sequences into frequency bands to calculate correlation.

The controller 120 may pad the dummy data to a read-out sequence acquired from the neuron resonance signal at a predetermined period, to have a predetermined sampling period. For example, the dummy data may be 0, a predetermined constant, or a value acquired by interpolating data contained in a corresponding digital sequence.

The controller 120 may set a certain resonance frequency of the neuron resonance signal and calculate correlation based on the set certain resonance frequency, a phase difference between the different repetition periods, and the plurality of different digital sequence data. Since specific exemplary embodiments have been described above, and thus, a description thereof will be omitted.

Figure 17:
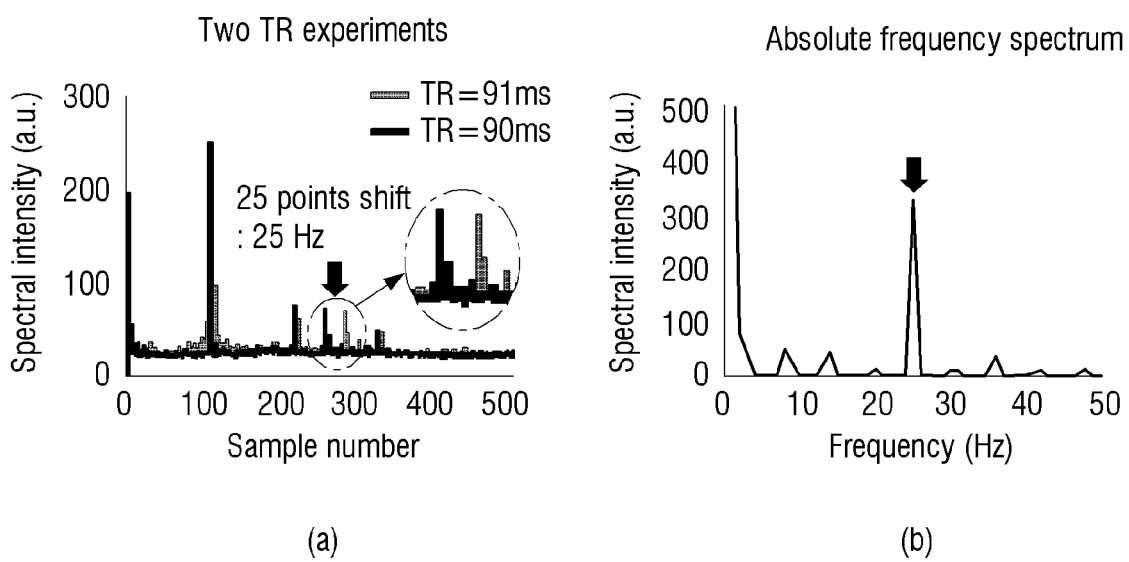
FIGS. 17 to 18 are diagrams illustrating results of a simulation of identifying a resonance frequency of neurons according to an exemplary embodiment of the present invention.
Figure 18:
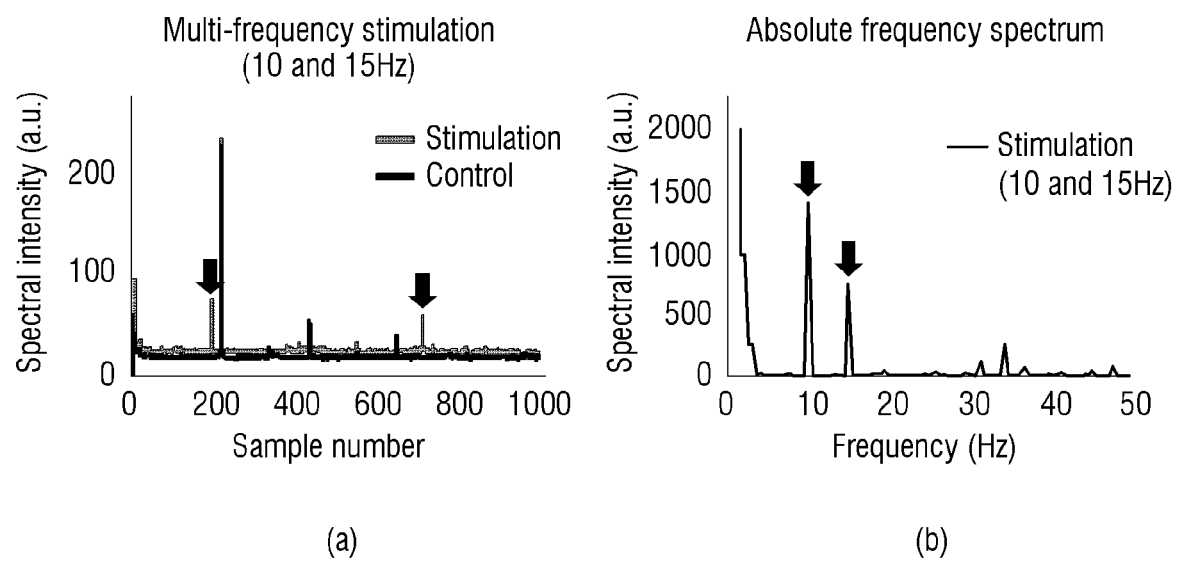

FIGS. 17 to 18 are diagrams illustrating results of simulation of identifying resonance frequencies of neurons according to an exemplary embodiment of the present invention.

Referring to FIG. 17, simulation results using two different TRs (90 ms and 91 ms) for one frequency component (25 Hz) of a neuron resonance signal are illustrated. As described above, since the maximum frequencies of the different TRs are different from each other, the process of matching the scales before superpositioning digital sequences of the two frequency regions may be performed. That is, the circles illustrated in FIG. 17A are displayed at different positions because the scales are different when the TR is 90 ms and when the TR is 91 ms, but both indicate energy values for the frequency component of 25 Hz. Referring to FIG. 17B, when the digital sequences in the frequency region according to the two different TRs are superimposed, other frequency components are suppressed and the 25 Hz frequency component is reinforced to display a relatively larger energy value.

Referring to FIG. 18, simulation results for two frequency components (10 Hz and 15 Hz) of the neuron resonance signal are shown. FIG. 18A shows sampling results of neuron resonance signals according to different TRs, and FIG. 18B shows results of superpositioning in the frequency region. Similar to FIG. 17, it can be seen that, when the digital sequences in the frequency region according to different TRs are superpositioned, two frequency components (10 Hz and 15 Hz) of the neuron resonance signal are expressed as a relatively larger energy value as illustrated in FIG. 18B.

The method of analyzing the neuron resonance signal according to various exemplary embodiments described above may be provided as a computer program product. The computer program product may include a software program itself or a non-transitory computer readable medium in which the software program is stored.

The non-transitory computer readable medium is a medium that semi-permanently stores data therein, rather than storing data for a second such as a register, a cache, a memory, and the like, and is readable by a device. In detail, various applications or programs described above may be stored and provided in the non-transitory computer readable medium such as a compact disk (CD), a digital versatile disk (DVD), a hard disk, a Blu-ray disk, a universal serial bus (USB), a memory card, a read only memory (ROM), or the like.

Although the exemplary embodiments have been illustrated and described hereinabove, the present disclosure is not limited to the above-mentioned specific exemplary embodiments but may be variously modified by those skilled in the art without departing from the scope and spirit of the present disclosure as disclosed in the accompanying claims. These modifications should also be understood to fall within the scope of the present disclosure. Further, using the exemplary embodiments of the present invention described above, those skilled in the art may easily make various changes and modifications within the scope of the present invention. The contents of each claim may be combined with other claims without a citing relationship within the scope that can be understood through this disclosure.

What is claimed is:

1. A method of detecting a neuron resonance signal, the method comprising:
    acquiring a plurality of first digital sequences corresponding to a first period by sampling a magnetic resonance signal of the neuron resonance signal according to the first period;
    acquiring a plurality of second digital sequences corresponding to a second period by sampling the magnetic resonance signal of the neuron resonance signal according to the second period, wherein the second period is different from the first period;
    calculating a correlation between the first digital sequences and the second digital sequences; and
    identifying a frequency component of the neuronal resonance signal based on the calculated correlation.

2. The method as claimed in claim 1, further comprising:
    identifying a frequency component in which a magnitude of the calculated correlation is equal to or greater than a predetermined magnitude, as the frequency component of the neuron resonance signal.

3. The method as claimed in claim 1, wherein the calculating comprises calculating the correlation by transforming each of the first and second digital sequences into a frequency band and superpositioning the first and second digital sequences of the transformed frequency bands.

4. The method as claimed in claim 1, wherein the calculating comprises calculating the correlation by convoluting the first digital sequences with the second digital sequences and transforming the convoluted first and second digital sequences into frequency bands.

5. The method as claimed in claim 1, wherein the calculating comprises setting a certain resonance frequency and calculating the correlation based on the set certain resonance frequency, a phase difference between each of the first and second periods, and data of each of the acquired first and second digital sequences.

6. The method as claimed in claim 1, further comprising:
    padding dummy data to each of the acquired first and second digital sequences to become a preset sampling period.

7. The method as claimed in claim 6, wherein the dummy data is 0, a predetermined constant, or a value acquired by interpolating data included in each of the first and second digital sequences.

8. The method as claimed in claim 1, wherein
    the first digital sequences are generated from a first read-out sequence representing a magnitude of the neuron resonance signal acquired at each read-out time point of the magnetic resonance signal according to the first period, and
    the second digital sequences are generated from a second read-out sequence representing a magnitude of the neuron resonance signal acquired at each read-out time point of the magnetic resonance signal according to the second period.

9. The method as claimed in claim 8, wherein the first digital sequences are sequences generated by padding first dummy data to the first read-out sequence to make the sampling period be a predetermined period, and the second digital sequences are sequences generated by padding second dummy data to the second read-out sequence such that the sampling period is the predetermined period.

10. The method as claimed in claim 9, wherein the calculating comprises calculating the correlation by superpositioning the first frequency spectrum of the first digital sequences and the second frequency spectrum of the second digital sequences.

11. The method as claimed in claim 9, wherein the calculating comprises convoluting the first digital sequences and the second digital sequences, transforming the convoluted first and second digital sequences into a frequency band, and calculating the correlation from a frequency spectrum of the convoluted first and second digital sequences.

12. The method as claimed in claim 9, wherein the predetermined period is equal to or smaller than a difference value between the first period and the second period.

13. A magnetic resonance imaging (MRI) signal processing apparatus comprising:
    an input unit receiving a magnetic resonance signal of a neuron resonance signal; and
    a controller acquiring a plurality of different digital sequences respectively corresponding to a plurality of different repetition periods by sampling the magnetic resonance signal of the neuron resonance signal according to each of the plurality of different repetition periods,
    wherein the controller:
        calculates correlation between the plurality of different digital sequences in a frequency band based on the plurality of different digital sequences, and
        identifies a frequency component of the neuronal resonance signal based on the calculated correlation.

14. A non-transitory computer-readable medium records a program executing:
    acquiring a plurality of first digital sequences corresponding to a first period by sampling a magnetic resonance signal of the neuron resonance signal according to the first period;
    acquiring a plurality of second digital sequences corresponding to a second period by sampling the magnetic resonance signal of the neuron resonance signal according to the second period, wherein the second period is different from the first period;

calculating a correlation between the first digital sequences and the second digital sequences; and identifying a frequency component of the neuronal resonance signal based on the calculated correlation.

* * * * *